(12) United States Patent
Crocker et al.

(10) Patent No.: US 8,181,529 B2
(45) Date of Patent: May 22, 2012

(54) SYSTEM AND METHOD FOR THE DETECTION OF FAULTS IN RAILS

(75) Inventors: Robert Lye Crocker, Derby (GB); Justin James Robert Stroud, Derby (GB)

(73) Assignee: Sperry Rail (International) Limited, Derby (GB)

( * ) Notice: Subject to any disclaimer, the term of this patent is extended or adjusted under 35 U.S.C. 154(b) by 668 days.

(21) Appl. No.: 12/294,232

(22) PCT Filed: Mar. 22, 2007

(86) PCT No.: PCT/GB2007/001070
§ 371 (c)(1), (2), (4) Date: Mar. 19, 2009

(87) PCT Pub. No.: WO2007/110613
PCT Pub. Date: Oct. 4, 2007

(65) Prior Publication Data
US 2009/0320603 A1    Dec. 31, 2009

(30) Foreign Application Priority Data

Mar. 24, 2006 (GB) .................................. 0605974.5

(51) Int. Cl.
*G01N 29/28* (2006.01)
(52) U.S. Cl. ............................................ 73/636; 73/644
(58) Field of Classification Search .................... 73/636, 73/620, 624, 625, 635, 639, 641
See application file for complete search history.

(56) References Cited

U.S. PATENT DOCUMENTS

| 3,028,753 | A |   | 4/1962 | Joy |
|---|---|---|---|---|
| 4,593,569 | A |   | 6/1986 | Joy |
| 5,419,195 | A |   | 5/1995 | Quinn |
| 5,522,265 | A |   | 6/1996 | Jaeggi |
| 5,777,891 | A | * | 7/1998 | Pagano et al. ............. 702/39 |
| 5,804,731 | A |   | 9/1998 | Jaeggi |
| 5,864,065 | A | * | 1/1999 | Prorok et al. ............. 73/622 |
| 6,116,184 | A | * | 9/2000 | Solayappan et al. ....... 118/50.1 |
| 6,258,733 | B1 | * | 7/2001 | Solayappan et al. ....... 438/785 |
| 6,401,044 | B1 | * | 6/2002 | Ibanez Rodriguez et al. .. 702/39 |
| 6,862,936 | B2 | * | 3/2005 | Kenderian et al. ......... 73/636 |
| 7,555,954 | B2 | * | 7/2009 | Pagano et al. ............. 73/620 |
| 7,934,703 | B2 | * | 5/2011 | Tomono et al. ............ 261/18.1 |

FOREIGN PATENT DOCUMENTS

| GB | 1322380 | 7/1973 |
|---|---|---|
| JP | 63003255 | 1/1988 |
| JP | 5142215 | 6/1993 |

* cited by examiner

*Primary Examiner* — J M Saint Surin
(74) *Attorney, Agent, or Firm* — McCormick, Paulding & Huber LLP

(57) ABSTRACT

A system (1) for the detection of defects in rails (12), the system comprising a source of ultrasonic waves for emitting ultrasonic waves onto a rail, a detector for detecting ultrasonic waves reflected or otherwise scattered by the rail or defects therein and a mist generator (3) arranged, in use, to expose one or both of the rail and source of ultrasonic wave to a mist of liquid, thus enabling the formation of an ultrasound-transmissive interface between the rail and the source of ultrasonic waves.

18 Claims, 1 Drawing Sheet

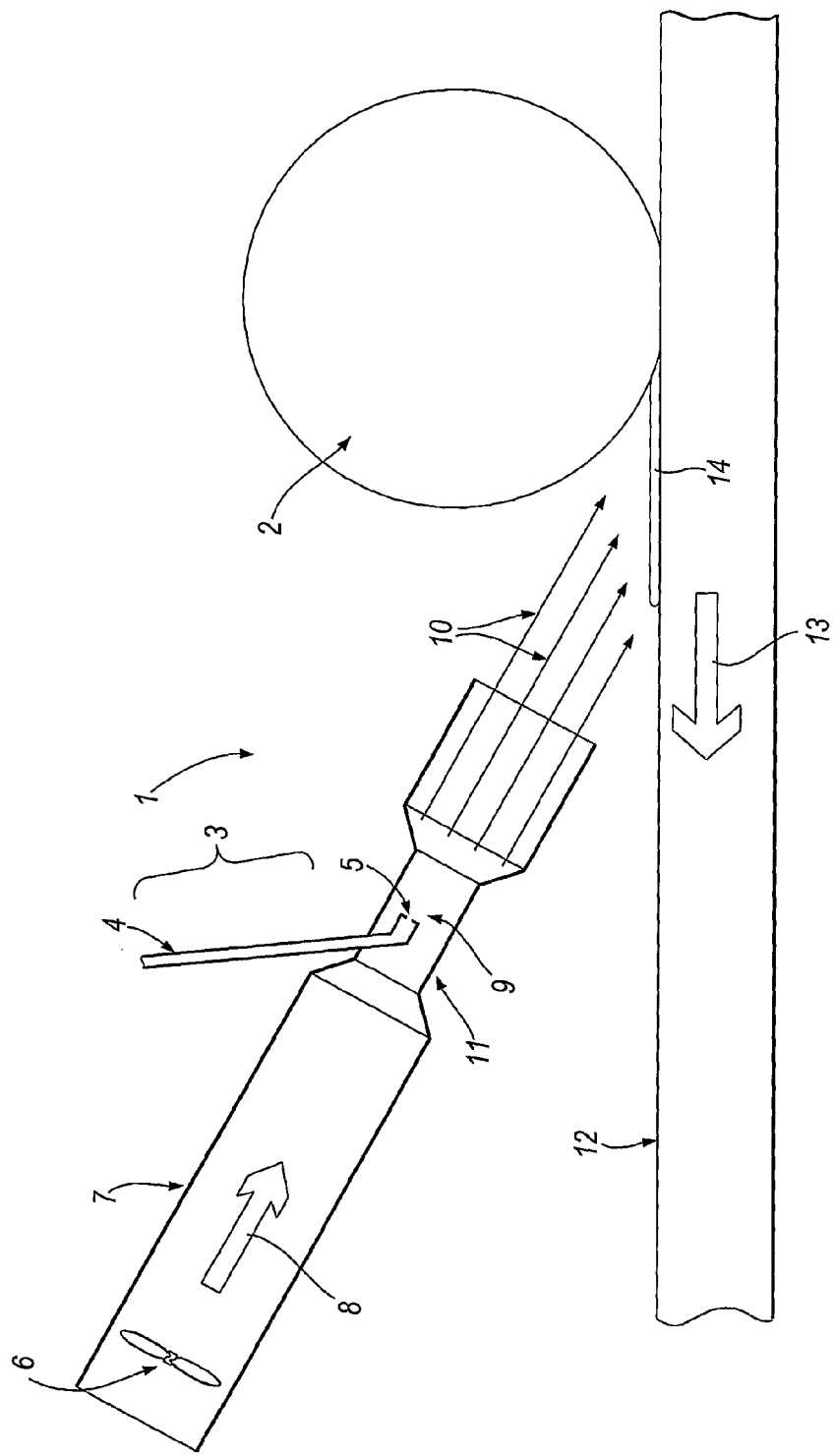

SYSTEM AND METHOD FOR THE DETECTION OF FAULTS IN RAILS

This application claims priority to International Patent Application No. PCT/GB2007/001070 filed on Mar. 22, 2007, which claims priority to Great Britain Patent Application No. 0605974.5 filed on Mar. 24, 2006.

This invention relates to the detection of rail defects, in particular defects in railway rails.

It is known to use ultrasound emitted and received by an ultrasonic transducer to inspect rails for defects. This technique relies on the transmission of ultrasound to and from the rail being inspected. A critical part of the path from the ultrasonic transducer is the interface between the transducer and the rail because the transmission of ultrasound is almost entirely blocked if an air layer is present between the rail and the transducer, even if that layer is microscopically thin. Consequently it is necessary to provide a means of excluding air from this interface region.

Air is usually excluded by putting water onto the rail, the water forming an ultrasound-transmissive layer between the rail and the transducer. Water is typically directed onto the rail either from the open end of a pipe or through a nozzle, the water being supplied to the rail by the action of gravity or by a pump. The process is often extremely inefficient in that far more water is dropped on the rail than is actually needed, most of the water spilling around and down the sides of the rail. This presents problems if the volume of water available is small. Furthermore, too much water around the sides of the transducer, (as opposed to between the transducer and rail) produces spurious ultrasonic signals that degrade the quality of testing. Problems of non-delivery of water to the desired place are also encountered when the relative velocity of the transducer and rail is high or when there is a high velocity cross-wind in the region of the transducer and rail. Undesired air pockets may form in regions of rail devoid of water.

The present invention mitigates against one or more of these problems.

In accordance with a first aspect of the present invention, there is provided a system for the detection of defects in rails, the system comprising a source of ultrasonic waves for emitting ultrasonic waves onto a rail, a detector for detecting ultrasonic waves reflected or otherwise scattered by the rail or defects therein and a mist generator arranged, in use, to expose one or both of the rail and source of ultrasonic waves to a mist of liquid, thus enabling the formation of an ultrasound-transmissive interface between the rail and the source of ultrasonic waves.

The mist generator may also be arranged, in use, to expose one or both of the rail and the detector of ultrasonic waves to a mist of liquid, thus enabling the formation of an ultrasound-transmissive interface between the rail and the detector of ultrasonic waves.

It has been found that exposure of a rail and/or the source of ultrasonic waves to a mist provides sufficient water to the rail to facilitate good transmission of ultrasound from the source to the rail and from the rail to the detector (if any such ultrasound is reflected or otherwise scattered by the rail). This provides a system that uses relatively little water which is important if the volume of water available is small or if testing is to be of lengthy duration.

The source of ultrasound waves and the detector of ultrasound waves are often provided in one component, such as an ultrasound transducer. The source and detector may, of course, be separate components. Such sources and detectors of ultrasonic waves are conventional to those skilled in the art.

A "mist of liquid" refers to a multiplicity of droplets of liquid, preferably in a carrier gas, such as air. The droplets of liquid are preferably small. The droplets may have a mean diameter of 4 mm or less. It is preferred that the droplets of liquid may have a mean diameter of 2 mm or less, more preferably 1 mm or less, further more preferably 500 microns or less, even further more preferably 200 microns or less. Advantageously the droplets may have a mean diameter of 150 microns or less, and more advantageously may have a mean diameter of 100 microns or less. The droplets forming the mist may have the size properties associated with the droplets of a mist generated by a perfume atomizer.

The detection of reflected (or otherwise scattered) ultrasonic waves may be indicative of defects in the rail under test. The detection of such reflected or scattered ultrasonic waves in the monitoring of rails is well known to the person skilled in the art.

The mist generator may typically comprise a conduit through which, in use, liquid is urged under pressure to an outlet, such as a small aperture. A mist is emitted from the outlet in use.

The liquid is typically water because it is cheap, forms a suitable ultrasound-transmissive film and is environmentally safe.

The system may typically be attached to, or form part of, a track defect detection vehicle.

The system is preferably capable of producing a spray or mist of liquid wherein the droplets therein have a high mean velocity relative to the source and detector of ultrasonic waves.

If the velocity of the droplets is too low, then the liquid may fail to form a suitable interface between the rail and the source of ultrasonic waves. This may occur, for example, if the system is mounted to a rail defect detecting vehicle traveling at high speed.

The velocity of the droplets may be sufficiently high so that a suitable interface is formed when the vehicle carrying the system is traveling at up to 30 m/s. The velocity of the droplets may be sufficiently high so that a suitable film is formed on the rail in high cross-winds, such as cross-winds of up to 30 m/s. The velocity of the droplets relative to the mist generator or optionally the source of ultrasonic waves may advantageously be greater than the velocity of the vehicle carrying the system or the velocity of any cross-wind.

The high mean droplet velocity may be generated by the mist generator providing droplets traveling at sufficiently high speeds.

Alternatively or additionally, the system may comprise a mist accelerator (distinct from the mist generator), arranged to accelerate the droplets forming the mist towards the rail subsequent to generation of the mist. The mist accelerator may be a means for generating air flow. The air flow may be used to carry the mist.

The mist accelerator may comprise a pump or fan, preferably upstream of the mist generator. A pump and fan are convenient means of generating airflow (and hence accelerating droplets carried by that airflow). The system may also comprise a baffle for directing air from the means for generating air flow to the mist generator. The baffle may be provided by a second conduit; the means for generating air flow may be disposed in the second conduit. The mist generator may be arranged, in use, to generate the mist in the second conduit. The second conduit may be provided with a constricted section. Such a constricted section is intended to produce a venturi effect i.e. the smaller cross-sectional area of the second conduit produces an increase in velocity of the air (and hence the velocity of the droplets carried in the air flow).

It is preferred that the mist generator is arranged, in use, to generate the mist in the constricted section of the second conduit.

The system may be arranged so that the droplets of the mist are deposited onto the rail forward of the source of ultrasonic waves. This is a convenient geometry for a vehicle traveling forward. The droplets of the mist may be emitted rearwardly of the mist generator.

In use, the means for generating air flow may draw in air at a temperature greater than ambient temperature. If the system is provided on, or is part of, a vehicle having an exhaust that, in use, emits air or other exhaust gas at a temperature higher than ambient temperature, the means for generating air flow may draw in said air or other exhaust gas.

Alternatively or additionally, the system may further comprise a heater arranged so that the means for generating air flow draws air into thermal contact with the heater.

The first conduit (or part thereof) may, in use, be in thermal contact with said air or exhaust gas at elevated temperature. This arrangement allows the liquid to be heated using warm air or exhaust gas used to propel the subsequently-produced mist.

The first conduit (or part thereof) may be located inside the second conduit. This enables the liquid to be heated by any warm air or exhaust gas in the second conduit and provides physical protection to the first conduit.

The liquid may be heated prior to formation of the mist. This may be achieved by providing a heater to heat the liquid.

In accordance with a second aspect of the present invention, there is provided a kit for assisting in detecting defects in rails, the kit comprising a means for generating a mist of liquid and one or both of (i) a bracket for mounting a mist generator on a track defect detection vehicle so that the mist generator is in spaced relation to a source of ultrasonic waves and (ii) a source of ultrasonic waves.

The kit may also comprise a detector for detecting ultrasonic waves.

The kit may also comprise a mist accelerator, such as that described above in relation to the system of the first aspect of the present invention.

The kit may also comprise those features described above in relation to the system of the first aspect of the present invention, such as the second conduit.

In accordance with a third aspect of the present invention, there is provided a method of detecting defects in rails, the method comprising:

(i) exposing one or both of a rail and a source of ultrasonic waves to a mist of liquid, thus enabling the formation of an ultrasound-transmissive interface between the rail and the source of ultrasonic waves (ii) passing ultrasonic waves through said interface onto said rail and (iii) sensing for ultrasonic waves reflected or otherwise scattered from said rail or defects therein.

The reflected or otherwise scattered ultrasonic waves sensed may be indicative of the absence or presence of one or more defects in the rail.

The droplets forming the mist may be accelerated towards the rail subsequent to generation of the mist. The velocity of the droplets may be sufficiently high so that a suitable film is formed on the rail when the vehicle carrying the system is traveling at up to 30 m/s. The velocity of the droplets may be sufficiently high so that a suitable film is formed on the rail in high cross-winds, such as cross-winds of up to 30 m/s.

The droplets may be carried towards the rail by a stream of air or other carrier gas, the stream of air or other carrier gas being directed towards the rail. Such a stream of air or other carrier gas may be generated by a fan or pump.

One or both of the air or other carrier gas and the liquid may be at greater than ambient temperature. The liquid may be heated prior to the generation of a mist.

The properties of the droplets used in the method of the third aspect of the present invention may be the same as those described above with respect to the system of the first aspect of the present invention. For example, the droplets may advantageously have a mean diameter of 150 microns or less, and more advantageously may have a mean diameter of 100 microns or less.

The method of the third aspect of the present invention may be performed using the system or kit of the first and second aspects of the present invention, respectively.

The present invention is now described by way of example only with reference to FIG. 1 which is a schematic representation of the system of the present invention.

FIG. 1 shows a system for the detection of defects in rails in accordance with the present invention. The system is denoted generally by reference numeral 1 and comprises a source of ultrasonic waves for emitting ultrasonic waves onto a rail 12, a detector for detecting ultrasonic waves reflected or otherwise scattered by the rail (or defects therein) and a mist generator 3 arranged, in use, to expose the rail and an ultrasonic transducer 2 to a mist of liquid, thus enabling the formation of an ultrasound transmissive interface between the rail 12 and the ultrasonic transducer 2, thus enabling the transmission of ultrasonic waves to and from the rail 12. The transducer 2 acts as a source and the detector of ultrasonic waves.

The system is attached to a wheeled railway vehicle that is traveling on the rails in the direction of arrow 13. The ultrasound transducer is substantially in contact with the rail, but, in the absence of water being sprayed onto the rail, air gaps may exist between the rail 12 and the transducer 2. Water is supplied between the rail 12 and the transducer 2 to provide an ultrasound-transmissive interface between the transducer and the rail 12.

The operation of the system is now discussed. Air is drawn into a second conduit 7 by a fan 6 (in this case, a centrifugal fan blower), the air being urged at speed along the conduit 7 as indicated by the arrow labeled 8. A first conduit 4 extends inside the second conduit downstream of the fan. Liquid (in this case, water) is carried from a reservoir (not shown) under the influence of a water pump (not shown) to a nozzle 5 located at the end of the first conduit 4. The pressure in the first conduit is about 3 to 4 bar; this pressure causes liquid to be urged out of the first conduit 4 as a mist into the region labeled 9. The nozzle 5 is a commercially-available mist-generating nozzle as used to form mists of water for watering plants (Gardena micro-mist nozzle, part no. 1371-20, available from Two Wests & Elliott Ltd, Chesterfield, UK, S41 9RH). The first conduit 4 comprises commercially-available tubing having an internal diameter of about 4 mm and an external diameter of about 6 mm. Once in this region 9, the droplets that form the mist are carried by air in a general direction shown by arrows 10 to form a film 14 of water on the surface of rail 12. Some water may also be deposited onto the surface of the transducer 2. The droplets are estimated to have a mean diameter of about 50 microns.

The second conduit 7 is provided with a constricted region 11 into which the mist is released. The constricted region 11 leads to the formation of a Venturi effect; the reduction in cross-sectional area of the second conduit 7 at the constriction causes the velocity of gas to increase. The nozzle 5 of the mist generator 3 is located in the constricted region 11 so that the droplets forming the mist are subjected to a high velocity carrier air stream. The second conduit 7 downstream of the constricted region 11 has the same internal diameter as the second conduit 7 upstream of the constricted region 11.

The water deposited on the rail 12 and possibly the transducer 2 forms an interface between the transducer 2 and rail 12 that is transmissive to ultrasonic waves. The ultrasonic waves pass from the transducer 2 through the water interface and into the rail 12. The ultrasonic waves generally pass uninterrupted through the rail 12 unless they are incident on some form of defect, such as a crack. Defects cause the ultrasonic waves to be reflected or otherwise scattered, the characteristics of the reflected or scattered ultrasonic waves being indicative of certain characteristics of the defect. For example, the time of receipt of a reflected signal may be indicative of the depth of the defect. The reflected or otherwise scattered waves are transmitted back through the rail 12, through the interface between the rail 12 and transducer 2, and into the transducer 2 where the reflected wave is detected.

The internal diameter of the second conduit 7 upstream and downstream of the constricted region 11 is about 50 mm.

The system of the present invention may be readily adapted for use in low temperature environments. For example, air may be passed over heating elements prior to being drawn into the second conduit 7. Alternatively or additionally, warm exhaust air may be taken from cooling units and the like and drawn into the second conduit 7 by the fan 6. The liquid in the first conduit 4 may also be heated. This may be achieved by locating the first conduit 4 inside the second conduit 7, if warm air is provided to the second conduit 7. Alternatively or additionally, a heater may be provided for heating the liquid prior to formation of the mist.

The present invention can deliver sufficient water to the rail to provide a suitable ultrasound-transmissive interface between the rail 12 and the transducer 2. Furthermore, the amount of water used is very low, thus reducing wastage and permitting smaller reservoirs to be used or permitting usage of longer duration. Furthermore, spurious ultrasonic signals are reduced because water does not, in normal use, usually collect in the area between the sides of the transducer and the rail where it is normally held by surface tension. The high velocity air continuously blows water away from this region thus precluding the creation of the spurious signals.

The high velocity of the air (and consequently the high velocity of the droplets in the mist) enables water to be delivered to the rail 12 even when the defect detecting vehicle is traveling at speeds of about 30 m/s. Furthermore, the high velocity of the droplets means that they are less susceptible from being blown-off course by cross-winds. The high velocity air can also form an effective shield around the water droplets so that when the droplets emerge from the conduit 7 they are relatively unaffected by external air movements either form the forward motion of the train or cross winds. The high velocity air also shapes the mist of droplets to avoid it becoming dispersed. This ensures that the droplets are effectively directed, with very little overspill down the sides of the transducer or rail.

Furthermore, it has been found that the high velocity water droplets wet the surface of the rail 12 very well. It is believed that the high velocity of the droplets causes the surface tension of the droplets to be broken when the droplets hit the rail.

The present invention is preferably used to detect defects in railway rails, but may be used to detect defects in other rails, such as tram rails.

The invention claimed is:

1. A system for the detection of defects in rails, the system comprising a source of ultrasonic waves for emitting ultrasonic waves onto a rail, a detector for detecting ultrasonic waves reflected or otherwise scattered by the rail or defects therein and a mist generator arranged, in use, to expose one or both of the rail and source of ultrasonic waves to a mist of liquid, thus enabling the formation of an ultrasound-transmissive interface between the rail and the source of ultrasonic waves, the system comprising a mist accelerator for accelerating the droplets forming the mist towards the rail subsequent to generation of the mist.

2. A system according to claim 1 wherein the source of ultrasonic waves for emitting ultrasonic waves and the detector for detecting ultrasonic waves are provided by an ultrasound transducer.

3. A system according to claim 1 wherein the mist generator comprises a first conduit through which, in use, liquid is urged under pressure to an outlet from which, in use, the mist is emitted.

4. A system according to claim 1 wherein the mist accelerator comprises a means for generating air flow.

5. A system according to claim 1 wherein the mist accelerator comprises a means for generating air flow and the system comprises a baffle for directing air from the means for generating air flow to the mist generator.

6. A system according to claim 1 wherein the mist accelerator comprises a means for generating air flow and the system comprises a baffle for directing air from the means for generating air flow to the mist generator, the baffle being provided by a second conduit, and the means for generating air flow is disposed in the second conduit.

7. A system according to claim 1 wherein the mist accelerator comprises a means for generating air flow and the system comprises a baffle for directing air from the means for generating air flow to the mist generator, the baffle being provided by a second conduit and the mist generator is arranged, in use, to generate the mist in the second conduit.

8. A system according to claim 1 wherein the mist accelerator comprises a means for generating air flow and the system comprises a baffle for directing air from the means for generating air flow to the mist generator, the baffle being provided by a second conduit, the second conduit being provided with a constricted section.

9. A system according to claim 1 wherein the mist accelerator comprises a means for generating air flow and, in use, the means for generating air flow draws in air at a temperature greater than ambient temperature.

10. A system according to claim 1 wherein the mist accelerator comprises a means for generating air flow and, in use, the means for generating air flow draws in air at a temperature greater than ambient temperature wherein the system is part of, or provided on, a vehicle having an exhaust that, in use, emits air or other exhaust gas at temperature higher than ambient temperature, and wherein the means for generating air flow draws in said air or other exhaust gas.

11. A system according to claim 1 wherein the mist accelerator comprises a means for generating air flow and, in use, the means for generating air flow draws in air at a temperature greater than ambient temperature the system further comprising a heater arranged so that the means for generating air flow draws air into thermal contact with the heater.

12. A system according to claim 1 wherein the mist generator comprises a first conduit through which, in use, liquid is urged under pressure to an outlet from which, in use, the mist is emitted and wherein the mist accelerator comprises a means for generating air flow and, the first conduit (or part thereof) is in thermal contact with said air at an elevated temperature.

13. A system according to claim 1 comprising a heater for heating the liquid.

14. A system according to claim 1 wherein the mist generator comprises a first conduit through which, in use, liquid is urged under pressure to an outlet from which, in use, the mist is emitted and wherein the mist accelerator comprises a means for generating air flow and the system comprises a baffle for directing air from the means for generating air flow to the mist generator, the baffle being provided by a second conduit wherein the first conduit (or part thereof) is located inside the second conduit.

15. A kit for assisting in detecting defects in rails, the kit comprising a means for generating a mist of liquid and one or both of (i) a bracket for mounting a mist generator on a track defect detection vehicle so that the mist generator is in spaced relation to a source of ultrasonic waves and (ii) a source of ultrasonic waves.

16. A kit according to claim 15 comprising a detector for detecting ultrasonic waves and a mist accelerator.

17. A method of detecting defects in rails, the method comprising:

(i) exposing one or both of a rail and a source of ultrasonic waves to a mist of liquid, thus enabling the formation of an ultrasound-transmissive interface between the rail and the source of ultrasonic waves;

(ii) passing ultrasonic waves through said interface onto said rail; and (iii) sensing for ultrasonic waves reflected or otherwise scattered from said rail or defects therein, the reflected or otherwise scattered ultrasonic waves sensed being indicative of the absence or presence of one or more defects in the rail, the droplets forming the mist being accelerated towards the rail subsequent to generation of the mist.

18. A method according to claim 17 wherein the droplets are carried towards the rail by a stream of air or other carrier gas, the stream of air or other carrier gas being directed towards the rail wherein one or both of the air or other carrier gas and the liquid is at a temperature greater than ambient temperature.

* * * * *